US00PP09122P

United States Patent [19]

Collicutt

[11] Patent Number: Plant 9,122

[45] Date of Patent: May 2, 1995

[54] SHRUB ROSE PLANT NAMED WINNIPEG PARKS

[75] Inventor: Lynn M. Collicutt, Morden, Canada

[73] Assignee: Her Majesty the Queen in Right of Canada, as represented by the Minister of Agriculture, Ottawa, Canada

[21] Appl. No.: 170,810

[22] Filed: Dec. 21, 1993

[51] Int. Cl.[6] ..... A01H 5/00

[52] U.S. Cl. ..... Plt./1

[58] Field of Search ..... Plt. 1, 22

[56] References Cited

PUBLICATIONS

Collicutt, 1992, 'Winnipeg Parks' Rose, HORTSCIENCE 27(10):1140–1141.

Haring, ed., 1986, MODERN ROSES 9, the American Rose Society, pp. 66–67, 206–207.

*Primary Examiner*—Howard J. Locker

*Attorney, Agent, or Firm*—Burns, Doane, Swecker & Mathis

[57] ABSTRACT

A new and distinct low-growing variety of shrub rose plant is provided which forms attractive relatively large medium-red blossoms which commonly are borne singly or in small clusters having reflexed sepals. The variety exhibits a slightly spreading growth habit, combines winter hardiness and everblooming characteristics, and commonly assumes a height of approximately 0.5 to 0.8 m. The new variety propagates well by the use of softwood stem cuttings, and is well adapted for growing as colorful ornamentation in the landscape.

5 Drawing Sheets

SUMMARY OF THE INVENTION

The new variety of shrub rose plant of the present invention was created by controlled artificial pollination at the Morden Research Station, Morden, Manitoba, Canada. The new variety is a complex hybrid that was developed from the *Rosa arkansana* hybrids Morden Cardinette and Cuthbert Grant, and Prairie Princess. Each of these named ancestors is non-patented in the United States. Prairie Princess commonly is classified as a shrub rose and has *Rosa laxs* and *Rosa spinosissima* its parentage. It is apparent that the new variety has three hardy species in its background. The parentage of the new variety is summarized in greater detail in FIG. 13.

Selective study resulted in the identification of a single plant of the new variety.

It was found that the new variety of shrub rose plant of the present invention possesses the following combination of characteristics:

(a) forms singly or in small clusters attractive relatively large medium-red blossoms which change to a dark pin-red coloration upon maturity having reflexed sepals;
(b) exhibits a slightly spreading growth habit;
(c) propagates well by the use of softwood stem cuttings;
(d) exhibits good winter hardiness; and
(e) is particularly well suited for growing in the landscape.

The new variety well meets the needs of the horticultural industry. It can be grown to advantage as attractive ornamentation in parks, gardens, public areas, and residential landsacpes. It is particularly well suited for growing in the landscape.

The new variety of the present invention can be readily distinguished from its Cuthbert grant and Morden cardinette parents each of which is non-patented in the United States. More specifically, the Cuthbert Grant variety exhibits darker red blossoms that generally correspond to Red-Purple Group 60A of R.H.S. Colour Chart, exhibits blossoms having a larger diameter, tends to lack reddish coloration on the young foliage, and forms a taller plant that is less compact. The Morden Cardinette variety tends to produce a greater number of petals per blossom, the blossom coloration is redder, the plant stature tends to be shorter, tends to lack reddish colornation on the young foliage, and the winter-hardiness tends to be less.

The characteristics of the new variety have been found to be homogeneous and stable and are strictly transmissible by asexual propagation using softwood stem cuttings conducted at Morden, Manitoba, Canada, from one generation to another.

The new variety has been named the Winnipeg Parks variety. The new variety was first available to the public in Canada during 1993 in conjunction with the centennial celebration of the City of Winnipeg Parks and Recreation Department, and was first available to the public in the United States during January, 1994.

BRIEF DESCRIPTION OF THE PHOTOGRAPHS

The accompanying photographs show, as nearly true as it is reasonably possible to make the same in color illustrations of this character, typical specimens of plant parts of the new variety. The rose plants of the new variety described herein were grown outdoors on their own roots at Morden, Manitoba, Canada.

FIG. 1 — illustrates an open medium-red flower.

FIG. 2 — illustrates a specimen of an entire plant while growing in the landscape;

FIG. 3 — illustrates a specimen of a bud as the sepals open;

FIG. 4 — illustrates a specimen of a bud in a further stage of opening wherein the sepals are reflexed;

FIG. 5 — illustrates a specimen of a flower when approximately $\frac{1}{4}$–$\frac{1}{2}$ open;

FIG. 6 — illustrates a specimen of a flower when approximately $\frac{1}{2}$–$\frac{3}{4}$ open;

FIG. 7 — illustrates a specimen of a flower when substantially fully open;

FIG. 8 — illustrates specimens of leaves having three, five and seven leaflets — plan view — obverse;

FIG. 9 — illustrates specimens of leaves having three, five and seven leaflets — plan view — reverse;

FIG. 10 — illustrates on the left a floral receptacle showing the arrangement of the stamens (sepals and petals removed), and on the right a floral receptacle showing the arrangement of the pistils (sepals, petals, and stamens removed);

FIG. 11 — illustrates a specimen of new growth;

FIG. 12 — illustrates a number of flowers in various stages of maturity while present on a plant growing in the landscape.

FIG. 13 — illustrates trhe parentage of the new variety.

DETAILED DESCRIPTION

Figure 1:
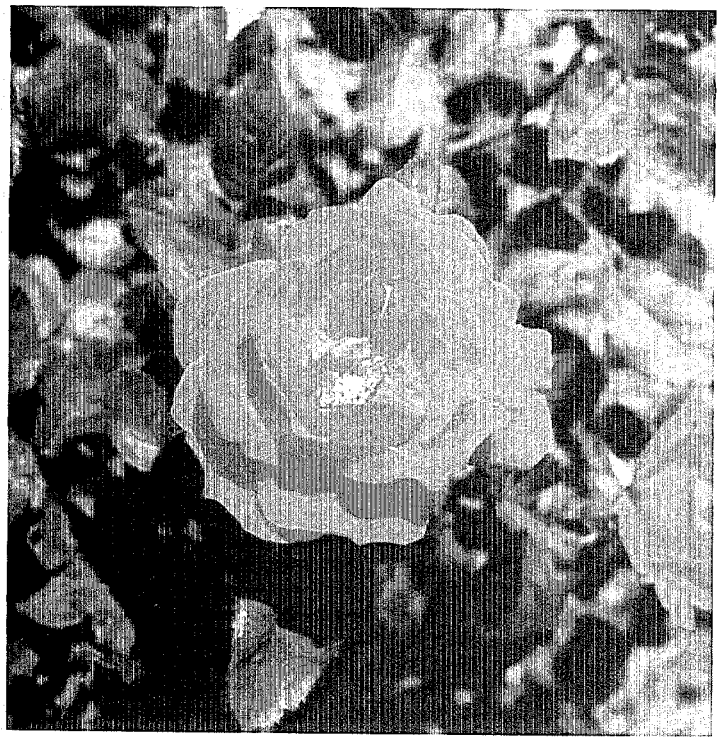
Figure 2:
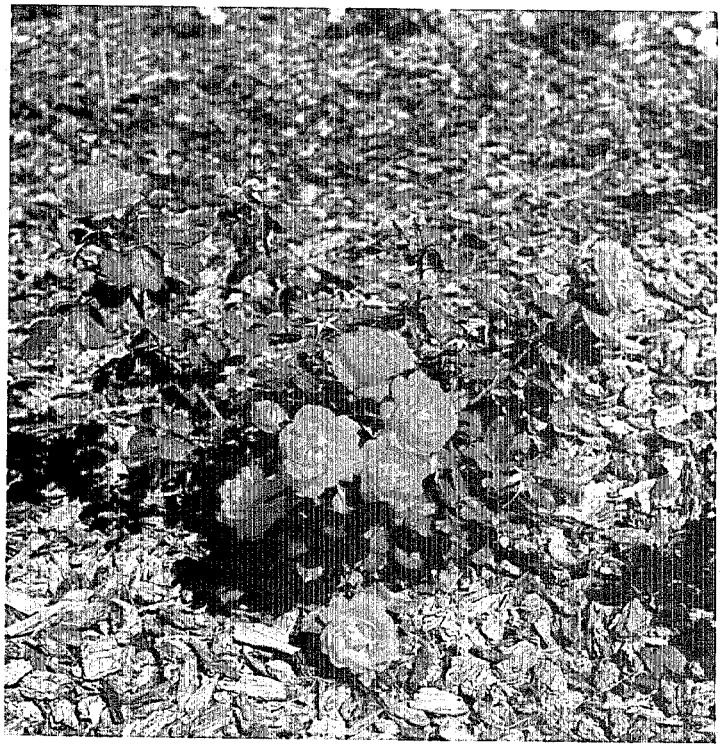
Figure 3:
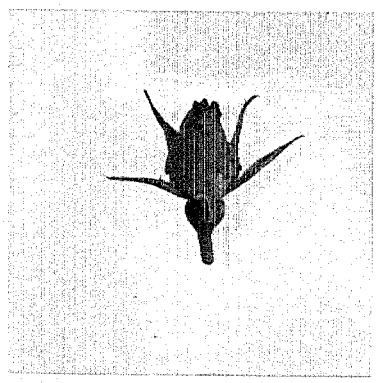
Figure 4:
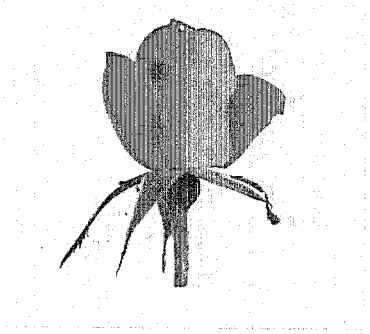
Figure 5:
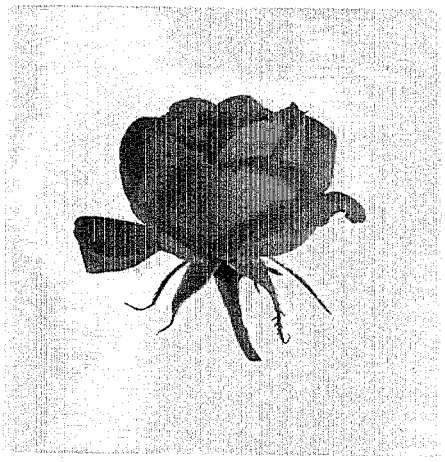
Figure 6:
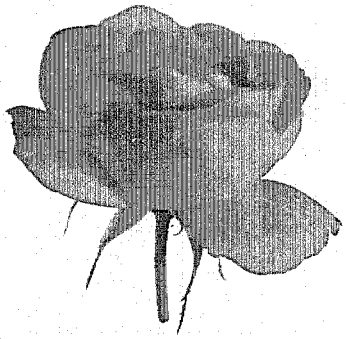
Figure 7:
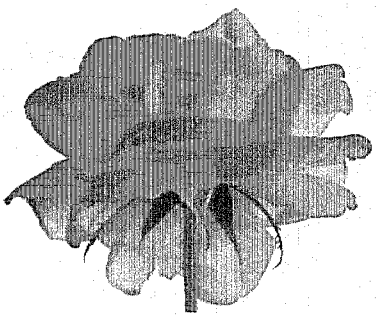
Figure 8:
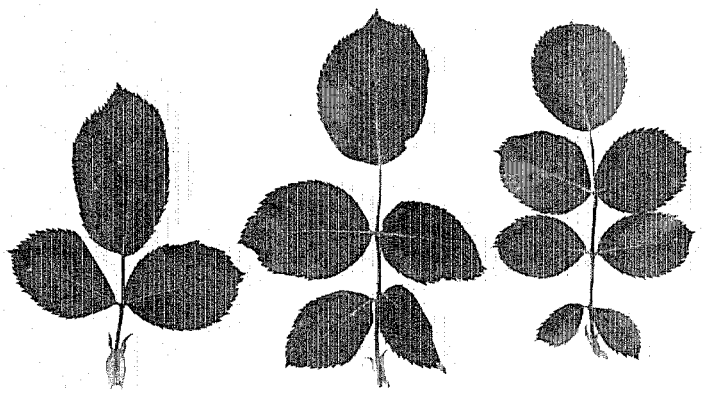
Figure 9:
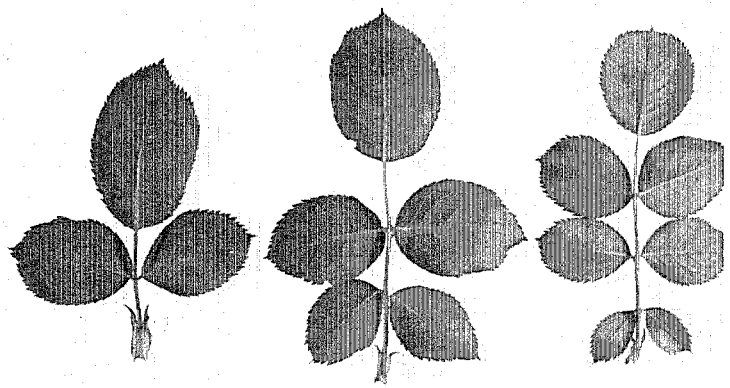
Figure 10:
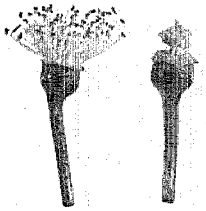
Figure 11:
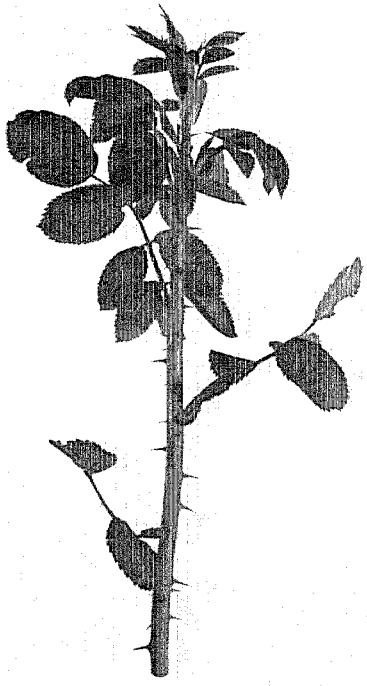
Figure 12:
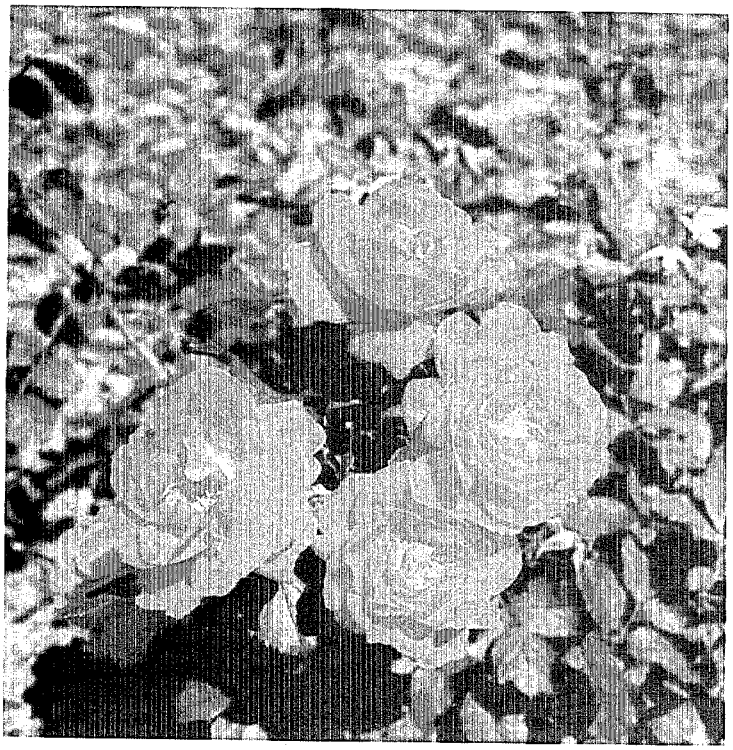
Figure 13:
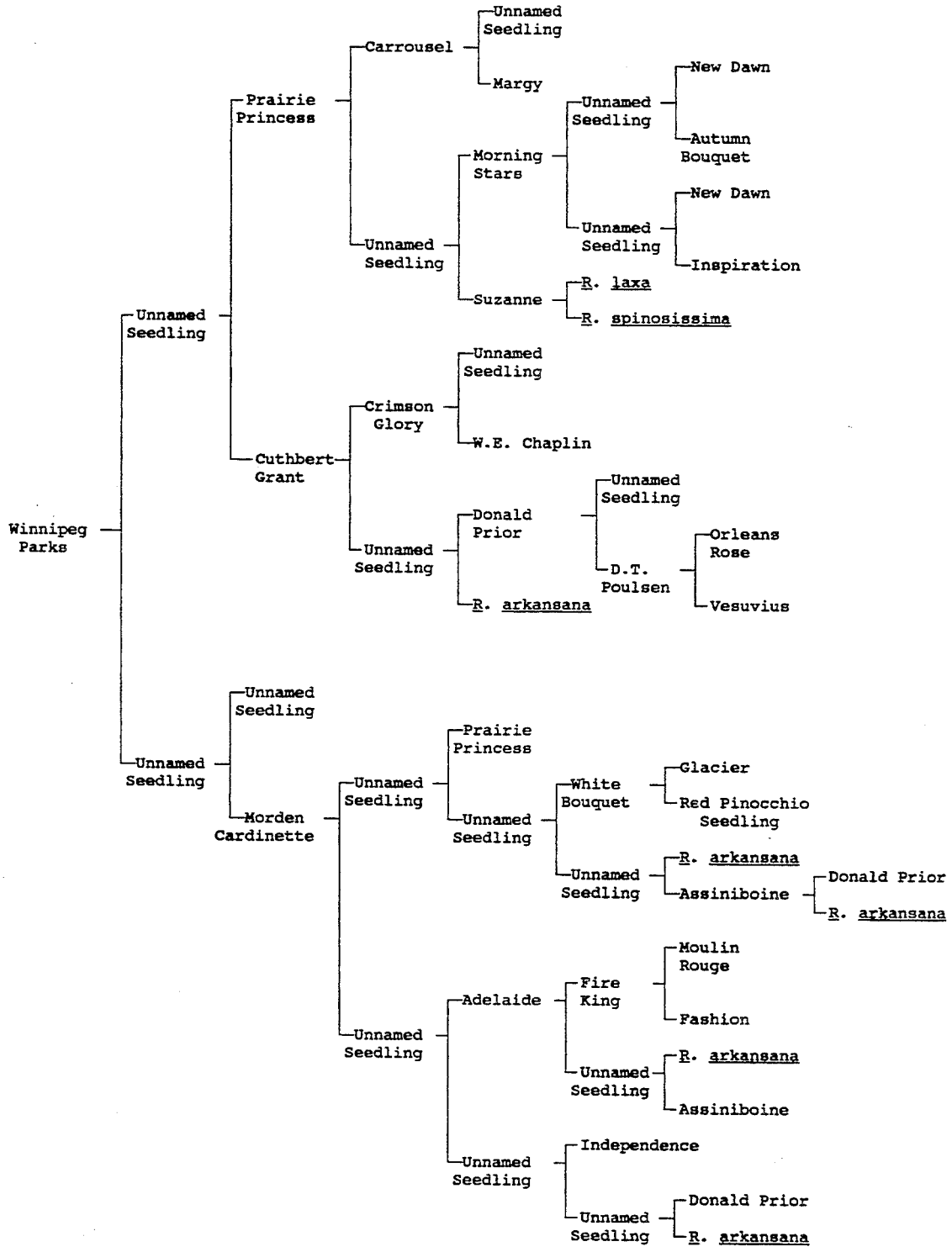

The chart used in the identification of colors is that of The Royal Horticultural Society (R.H.S. Colour Chart). Common color terms are to be accorded their ordinary dictionary significance. The description is based on the observation of specimens of the new variety while grown outdoors on their own roots at Morden, Manitoba, Canada.

Class: Shrub.

Plant:

*Height.*—Approximately 50 to 80 cm. on average.

*Width.*—Approximately 50 cm. on average.

*Habit.*—Slightly spreading.

Branches:

*Color.*—Young stems: yellow green, Yellow-Green Group 144A and slightly shaded with reddish coloration during cooler growing conditions. Mature stems: yellow green to green, Green group 138B to Yellow-Green Group 146B with slight grey coloration.

*Prickles.*—Shape: slightly concave on upper edge, moderately concave on under edge, and the base is slightly dilated. The prickles tend to angle downwards. Size: medium — 0.4 to 0.6 cm., and narrow in width to almost linear. Quantity: fed to moderately numerous. Color: dark reddish with purple tip. Red coloration tends to be more intense along the upper edge. Red-Purple group 58A to 60A. Prickles on mature stems have a grey-brown base that approximately Grey-Brown Group 199D. The prickles change to a tan coloration on older stems that approximates Greyed-Orange Group 165D.

Leaves: Compound and pinnate.

*Stipules.*—Adnate, fairly narrow and linear, with hairs along edge and slightly glandular, auricles are erect.

*Petioles.*—Upper surface: green in coloration with slightly glandular edge. Reddish in coloration in cool weather. Under surface: green to yellowish green in coloration.

*Petiolules.*—Very short or non-existent.

*Foliage.*—Number: 3, 5 or 7. Shape: oval to rounded base, some uneven, slightly acute tip, obtuse base. Serrations: single and fairly regular. General appearance: semi-dull. Color: (young foliage): upper surface: medium green, Green Group 137A to Yellow-Green Group 147A, some leaves exhibit reddish shading that approximates Greyed-Purple Group 184A. under surface: medium green, Yellow-Green Group pb 147B some leaves exhibit reddish shading that approximates Greyed-Purple Group 184A. Color (adult foliage): upper surface: Green Group 137A to Yellow-Green Group 147A. under surface: Yellow-Green Group 147B.

*Rachis.*—A few small pickles are present on the under surface, slightly grooved, a few small white hairs are present along the ridge, and a few glands may be disposed along the outer two ridges at the top.

Inflorescence:

*Number of flowers.*—Usually 1 to 8 per stem.

*Peduncle.*—Erect, approximately 3 cm in length, reddish green, small hairs are present at a sparse frequency, and slightly to moderately glandular.

*Sepals.*—Upper surface: white tomentose, greenish in coloration, may also bear a slightly reddish-purple coloration. Under surface: yellow green in coloration, may also bear a slightly reddish-purple coloration, slightly glandular. Appendages: one or two sepals commonly have a very small linear outgrowth on the side, and one or two sepals commonly have no appendages or weak sepal appendages. Length: initally of approximately the same length as the bud after which the petals elongate and exceed the length of the sepals. Shape: tapering to a long narrow tip, commonly one sepal has a leaf-like tip, and the others commonly have an attenuate tip.

Buds.—Shape: slender, tapering to a point. Length: approximatrely 2.5 to 3 cm. on average outside the calyx at the opening of the sepals. Coloring upon opening: medium red, closest to Red Group 53C.

*Flower.*—Shape: cup-shaped with outer petals reflexed back very slightly. The center opens to expose the anthers and stigmas. Diameter: approximately 7 to 10 cm. on average, and substantially round when viewed from above. Color (when blooming): dark pink-red, Red Group 53B to 53C on the upper surface and Red-Purple Group 57C on the under surface. Color (at end of blooming): ages to dark pink Red Purple Group 57A. The petals have a white base. Fragrance: slight. Petal form: circular to broadly circular, to broadly obovate. Some petals slightly notched, the outer one or two petals are notched and usually exhibit a white midrib, often a few inner petals also have a white midrib and may be notched. Petal number: approximately 22 on average. Petal drop: blossoms commonly last approximately 5 to 7 days and the petals drop off fairly cleanly. Anthers: gold in coloration, Yellow-Orange Group 20A to 20B. Pollen: yellow and normal for the class. Filaments: yellow-green fading to white in coloration. Stigmas: cream to light yellow in coloration. Styles: hairy along the length, slightly reddish in coloration below the stigma, located below the anthers, and commonly not attached to each other. Receptacle: medium green, may also bear a reddish-purple coloration, at the dehiscence of the anthers in longitudinal section it is globular and in the shape of a cup, and forms fertile hips with the sepals often being retained in a somewhat reflexed configuration often in the absence of dehiscence; however, sometimes a few sepals will dehisce.

Development:

*Vegetation.*—Intermediate vigor.

*Blossoming.*—Intermediate.

*Hardiness.*—Survives consistently in the landscape without protection on the Canadian prairies (Zone 3 of Ouellet and Sherk 1967).

*Resistance to diseases.*—Moderate.

Field resistance to powdery mildew (*Sphaerotheca pannosa*) and rust (Phragmidium) is good with 0 to 10 percent of the leaves infected, while field resistance to blackspot (*Diplocarpon rosae*) is fair to good with approximately 25 percent of the leaves infected. Resistance levels for both diseases are similar to those of the Morden Blush variety (U.S. Plant Pat. No. 8,054). The resistance to powdery mildew and rust was rated during June and July, and the blackspot resistance was rated during August and September.

I claim:

1. A new and distinct varietyt of shrub rose plant characterized by the following combination of characteristics:

(a) forms singly or in small clusters attractive relatively large medium-red blossoms which change to a dark pink-red coloration upon maturity having reflexed sepals;

(b) exhibit a slightly spreading growth habit;

(c) propagates well by the use of softwood stem cuttings;

(d) exhibits good winter hardiness; and (e) is particularly well suited for growing in the landscape;

substantially as herein shown and described.

* * * * *